US010734097B2

(12) United States Patent
Lee et al.

(10) Patent No.: US 10,734,097 B2
(45) Date of Patent: Aug. 4, 2020

(54) ATOMIC STRUCTURE OPTIMIZATION

(71) Applicant: Synopsys, Inc., Mountain View, CA (US)

(72) Inventors: Kyuho Lee, Albany, CA (US); Yong-Seog Oh, Pleasanton, CA (US); Ashutosh Kumar, San Jose, CA (US); Pratheep Balasingam, San Jose, CA (US)

(73) Assignee: Synopsys, Inc., Mountain View, CA (US)

( * ) Notice: Subject to any disclaimer, the term of this patent is extended or adjusted under 35 U.S.C. 154(b) by 0 days.

(21) Appl. No.: 16/122,711

(22) Filed: Sep. 5, 2018

(65) Prior Publication Data

US 2019/0005202 A1 Jan. 3, 2019

Related U.S. Application Data

(63) Continuation-in-part of application No. 14/928,615, filed on Oct. 30, 2015, now Pat. No. 10,078,735.

(51) Int. Cl.
| | |
|---|---|
| *G06F 9/00* | (2006.01) |
| *G06F 17/50* | (2006.01) |
| *G16C 10/00* | (2019.01) |
| *G16C 20/90* | (2019.01) |
| *G16C 60/00* | (2019.01) |

(Continued)

(52) U.S. Cl.
CPC .............. *G16C 10/00* (2019.02); *G06F 30/20* (2020.01); *G06F 30/367* (2020.01); *G16C 20/90* (2019.02); *G16C 60/00* (2019.02); *G06F 2111/10* (2020.01); *G06F 2119/18* (2020.01)

(58) Field of Classification Search
CPC .... G06F 17/18; G06F 19/701; G06F 17/5009; G06F 17/5018; G06F 17/5022; G06F 17/5036; G06F 17/10; G06F 17/505
USPC ........... 702/27; 703/2, 13; 716/53, 106, 108, 716/134; 700/266
See application file for complete search history.

(56) References Cited

U.S. PATENT DOCUMENTS

| | | |
|---|---|---|
| 5,246,800 A | 9/1993 | Muray |
| 5,472,814 A | 12/1995 | Lin |

(Continued)

FOREIGN PATENT DOCUMENTS

| | | |
|---|---|---|
| CN | 108369610 A | 8/2018 |
| WO | 00-72185 A2 | 11/2000 |

(Continued)

OTHER PUBLICATIONS

U.S. Appl. No. 15/024,009—Final Office Action dated Nov. 18, 2016, 24 pages.

(Continued)

*Primary Examiner* — John H Le
(74) *Attorney, Agent, or Firm* — Haynes Beffel & Wolfeld, LLP; Andrew L. Dunlap; Paul A. Durdik

(57) ABSTRACT

Computer system provided with a control module for controlling ab initio atomic structure modules for simulating the behavior of structures and materials at multiple scales with different modules, for purposes of evaluating such structures and materials for use in integrated circuit devices. The computer system can simulate the behavior of structures and materials at atomic scale with parameters or a configuration that varies across iterative transformations.

19 Claims, 10 Drawing Sheets

(51) Int. Cl.
G06F 30/20 (2020.01)
G06F 30/367 (2020.01)
G06F 111/10 (2020.01)
G06F 119/18 (2020.01)

(56) References Cited

U.S. PATENT DOCUMENTS

| | | | |
|---|---|---|---|
| 5,702,847 | A | 12/1997 | Tarumoto et al. |
| 6,057,063 | A | 5/2000 | Liebmann et al. |
| 6,096,458 | A | 8/2000 | Hibbs |
| 6,685,772 | B2 | 2/2004 | Goddard, III et al. |
| 7,448,022 | B1 | 11/2008 | Ram et al. |
| 7,756,687 | B2 | 7/2010 | Hwang et al. |
| 8,112,231 | B2 | 2/2012 | Samukawa |
| 8,453,102 | B1 | 5/2013 | Pack et al. |
| 8,454,748 | B2 | 6/2013 | Iwaki et al. |
| 8,555,281 | B1 | 10/2013 | van Dijk et al. |
| 8,572,523 | B2 | 10/2013 | Tuncer et al. |
| 8,626,480 | B2 | 1/2014 | Chang et al. |
| 9,177,095 | B1 | 11/2015 | Krishnan et al. |
| 9,858,365 | B2 * | 1/2018 | Klimeck ............. G06F 17/5009 |
| 2002/0142495 | A1 | 10/2002 | Usujima |
| 2003/0217341 | A1 | 11/2003 | Rajsuman et al. |
| 2003/0217343 | A1 | 11/2003 | Rajsuman et al. |
| 2004/0063225 | A1 | 4/2004 | Borden et al. |
| 2004/0067355 | A1 | 4/2004 | Yadav et al. |
| 2005/0223633 | A1 | 10/2005 | Sankaranarayanan |
| 2005/0278124 | A1 | 12/2005 | Duffy et al. |
| 2005/0281086 | A1 | 12/2005 | Kobayashi et al. |
| 2006/0038171 | A1 | 2/2006 | Hasumi et al. |
| 2006/0101378 | A1 | 5/2006 | Kennedy et al. |
| 2007/0177437 | A1 | 8/2007 | Guo |
| 2007/0185695 | A1 | 8/2007 | Neumann |
| 2007/0265725 | A1 | 11/2007 | Liu et al. |
| 2008/0052646 | A1 | 2/2008 | Tuncer et al. |
| 2008/0147360 | A1 | 6/2008 | Fejes et al. |
| 2009/0032910 | A1 | 2/2009 | Ahn et al. |
| 2010/0070938 | A1 | 3/2010 | Wang et al. |
| 2011/0131017 | A1 | 6/2011 | Cheng et al. |
| 2011/0161361 | A1 | 6/2011 | Csanyi et al. |
| 2011/0231804 | A1 | 9/2011 | Liu et al. |
| 2011/0246998 | A1 | 10/2011 | Vaidya et al. |
| 2011/0313748 | A1 | 12/2011 | Li |
| 2012/0228615 | A1 | 9/2012 | Uochi |
| 2012/0232685 | A1 | 9/2012 | Wang et al. |
| 2013/0139121 | A1 | 5/2013 | Wu et al. |
| 2014/0180645 | A1 | 6/2014 | Lee et al. |
| 2015/0088473 | A1 | 3/2015 | Liu et al. |
| 2015/0088481 | A1 | 3/2015 | Liu et al. |
| 2015/0089511 | A1 | 3/2015 | Smith et al. |
| 2015/0120259 | A1 | 4/2015 | Klimeck et al. |
| 2016/0171139 | A1 | 6/2016 | Tago et al. |
| 2016/0335381 | A1 | 11/2016 | Liu et al. |

FOREIGN PATENT DOCUMENTS

| | | | |
|---|---|---|---|
| WO | 01-08028 | A2 | 2/2001 |
| WO | 02-058158 | A2 | 7/2002 |
| WO | 2013-133770 | A1 | 9/2013 |

OTHER PUBLICATIONS

PCT/US2016/059402—International Search Report and Wirtten Opinion dated Feb. 17, 2017, 9 pages.
Kresse et al., "Vienna Ab-initio Simulation Package, VASP the GUIDE", Apr. 23, 2009.
Opalka et al., "First Principles Investigation of PEMFC Catalyst Alloy Surface Hydration and Oxidation," ECS Transactions, vol. 11, No. 1, pp. 739-748, Sep. 28, 2007.
Michalkova et al., "A Quest for Efficient Methods of Disintegration of Organophosphorus Compounds: Modeling Adsorption and Decomposition Processes," Molecular Materials with Specific Interactions—Modeling and Design, ISBN 978-4020-5371-9, pp. 565-592, 2007.
Baker, Jon, "Molecular Structure and Vibrational Spectra," Handbook of Computational Chemistry, ISBN 978-94-007-0710-8, pp. 293-359, 2012.
Nagel, et al., "Spice (Simulation Program with Integrated Circuit Emphasis)", Memorandum No. ERL-M382, Electronics Research Laboratory, College of engineering, University of California, Berkeley, CA USA, (Apr. 12, 1973), 55 pages.
U.S. Appl. No. 14/906,543—Office Action dated Jun. 17, 2016, 26 pages.
U.S. Appl. No. 15/081,735—Office Action dated Dec. 13, 2016, 30 pages.
PCT/US2014/057840—International Preliminary Report on Patentability dated Mar. 29, 2016, 5 pages.
U.S. Appl. No. 15/081,735—Response to Office Action dated Jun. 15, 2016 filed Nov. 15, 2016, 18 pages.
PCT/US2014/057803—International Search Report and Written Opinion dated Nov. 28, 2014, 14 pages.
U.S. Appl. No. 15/024,009—Office Action dated Jul. 21, 2016, 24 pages.
U.S. Appl. No. 15/024,009—Response to Office Action dated Jul. 21, 2016 filed Nov. 1, 2016, 38 pages.
U.S. Appl. No. 15/024,009—Preliminary Amendment filed Mar. 22, 2016, 9 pages.
Martin-Bragado et al., "Modeling charged defects, dopant diffusion and activation mechanisms for TCAD simulations using Kinetic Monte Carlos," Nuclear Instruments and Methods in Physics Research Section B: Beam Interactions with Materials and Atoms, 253:1, 18 pages, Dec. 2006.
Nagel, Laurence W., "SPICE2: A Computer Program to Simulate Semiconductor Circuits", Memorandum No. UCB/ERL-M520, Electronics Research Laboratory, College of Engineering, University of California, Berkeley, CA USA, (May 9, 1975), 431 pages.
Synopsys, Sentaurus TCAD, Industry-Standard Process and Device Simulators, Datasheet (2012), 4 pages.
Yip, S. (ed.), Handbook of Materials Modeling, 565-588. c 2005 Springer.
U.S. Appl. No. 14/497,681—Response to Office Action dated Aug. 25, 2016 filed Jan. 24, 2017, 10 pages.
U.S. Appl. No. 14/906,543—Response to Office Action dated Jun. 17, 2016 filed Dec. 19, 2016, 12 pages.
U.S. Appl. No. 14/906,543—Final Office Action dated Feb. 10, 2017, 16 pages.
U.S. Appl. No. 14/906,543—Preliminary Amendment dated Jan. 20, 2016, 8 pages.
U.S. Appl. No. 15/081,735—Response to Office Action dated Dec. 13, 2016, filed Mar. 13, 2017, 10 pages.
Lee et al., "Area and Volume Measurements of Objects with Irregular Shapes Using Multiple Silhouettes," Optical Engineering 45(2), Feb. 2006, 11 pages.
Keneti, et al., "Determination of Volume and Centroid of Irregular Blocks by a Simplex Integration Approach for Use in Discontinuous Numerical Methods," Geomechanics and Geoengineering: An International Journal, vol. 3, No. 1, Mar. 2008, pp. 79-84.
U.S. Appl. No. 15/081,735—Notice of Allowance dated Mar. 29, 2017, 17 pages.
U.S. Appl. No. 14/928,615—Office Action dated Jan. 9, 2018, 28 pages.
U.S. Appl. No. 14/928,615—Supplemental Office Action dated Jan. 18, 2018, 5 pages.
U.S. Appl. No. 14/928,615—Notice of Allwoance dated May 14, 2018, 10 pages.
U.S. Appl. No. 14/928,615—Respopnse to Restriction Requirement Oct. 13, 2017, filed Dec. 8, 2017, 17 pages.
U.S. Appl. No. 14/928,615—Response to Office Action dated Jan. 9, 2018, filed Mar. 28, 2018, 12 pages.
PCT/US2016/059402—International Preliminary Report on Patentability dated May 11, 2018, 11 pages.
PCT/US2014/057637—International Search Report and Written Opinion dated Jan. 5, 2015, 12 pages.
Wang, Yan, "Multiscale Simulations", Georgia Institute of Technology, available at http://www-old.me.gatech.edu/~ywang/CANE/lect05_MultiscaleSims_yanwang.pdf, (dated May 14-16, 2012), 40 pages.

(56) References Cited

OTHER PUBLICATIONS

Braunstein, Rubin, et al., "Intrinsic Optical Absorption in Germanium-Silicon Alloys", Physical Review, vol. 109, No. 3, (Feb. 1, 1958), pp. 695-710.
Sant, Saurabh, et al., "Band gap bowing and band offsets in relaxed and strained Si1-xGex alloys by employing a new nonlinear interpolation scheme", published online Jan. 18, 2013, Journal of Applied Physics, vol. 113, pp. 033708-1 through 033708-10.
Uppal, S., et al., "Diffusion of boron in germanium at 800-900° C.", Journal of Applied Physics, vol. 96, No. 3, (Aug. 1, 2004), pp. 1376-1380.
Haddara, Y.M., et al., "Accurate measurements of the intrinsic diffusivities of boron and phosphorus in silicon", Applied Physics Letters, vol. 77, No. 13, (Sep. 25, 2000), pp. 1976-1978.
Uppal, S., et al., "Diffusion of ion-implanted boron in germanium", Journal of Applied Physics, vol. 90, No. 8, (Oct. 2001), 4293-4295.
Stadler, J., et al., "IMD: a Software Package for Molecular Dynamics Studies on Parallel Computers", International Journal of Modren Physics C, vol. 8, No. 5, (Oct. 1997), pp. 1131-1140.
Refson, Keith, "Moldy: a portable molecular dynamics simulation program for serial and parallel computers", Computer Physics Communications, vol. 126, issue 3, (Apr. 11, 2000), pp. 310-329.
Smith, W., et al., "DL_POLY: Application to molecular simulation", Molecular Simulation, vol. 28, Issue 5, (May 5, 2002), pp. 385-471.
Smith, W., and Forester, T.R., "DL_POLY_2.0: A general-purpose parallel molecular dynamics simulation package", Journal of Molecular Graphics, vol. 14, Issue 3, (Jun. 1996), pp. 136-141.
Nieminen, Risto M., "From atomistic simulation towards multiscale modelling of materials", J. Phys.: Condens. Matter, (published Mar. 8, 2002), vol. 14, pp. 2859-2876.
"Simulation of Random Dopant Fluctuation Effects in TCAD Sentaurus", TCAD News, Dec. 2009, Synopsys, Mountain View, CA, USA, 4 pages.
Yu, P.Y., and Cardona, M., "2. Electronic Band Structures", Fundamentals of Seminconductors, Graduate Texts in Physics, 4th ed., Springer-Verlag Berlin Heidelberg, (2010), pp. 17-106.
"ITRS, International Technology Roadmap for Semiconductors, 2012 Update", (2012), available at http://www.itrs.net/Links/2012ITRS/2012Chapters/2012Overview.pdf, 76 pages.
"Sentaurus TCAD" datasheet, Synopsys, Inc., Mountain View, CA USA, May 2012, 4 pages.
"ITRS, 2012 Overall Roadmap Technology Characteristics (ORTC) Tables", International Technology Roadmap for Semiconductors, 2012, availalbe at http://www.itrs.net/Links/2012ITRS/2012Tables/ORTC_2012Tables.xlsm, visited Oct. 14, 2013, 39 pages.
Hansen, Stephen E., "SUPREM-III User's Manual, Version 8628", (Aug. 1986), available from http://www-tcad.stanford.edu/tcad/programs/suprem3man.pdf, visited Oct. 14, 2013, 186 pages.
"Sentaurus Device" datasheet, Synopsys, Inc., Mountain View, CA, USA, Feb. 2007, 8 pages.
Dunham, Scott T., "A Quantitative Model for the Coupled Diffusion of Phosphorus and Point Defects in Silicon", J. Electrochem. Soc., vol. 139, No. 9, (Sep. 1992), pp. 2628-2636.
Skinner, Richard D., editor, "Basic Integrated Circuit Manufacturing", section 2 of "Technology Reference Manual", ICE, Integrated Circuit Engineering, (1993), 112 pages.
Quarles, Thomas Linwood, "Analysis of Performance and Convergence Issues for Circuit Simulation", Memorandum No. UCB/ERL M89/42, Electronics Research Laboratory, College of Engineering, University of California, Berkeley, CA USA, (Apr. 1989), 142 pages.
Dunga, Mohan V., et al., "BSIM4.6.0 MOSFET Model—User's Manual", Department of Electrical Engineering and Computer Sciences, University of California, Berkeley, CA USA, 2006, 201 pages.
Burke, Kieron, and friends, "The ABC of DFT", Department of Chemistry, University of California, Irvine, CA, (Apr. 10, 2007), available at http://chem.ps.uci.edu/~kieron/dft/book/, 104 pages.
Luisier, Mathieu, "Quantum Transport Beyond the Effective Mass Approximation", Diss. ETH No. 17016, 2007, 150 pages.
Taur, Y., "CMOS design near the limit of scaling", IBM J. Res. & Dev., vol. 46, No. 2/3, Mar./May 2002, pp. 213-212.
Luisier, Mathieu, "Quantum Transport for Engineers Lecture 4: Wave Function (WF) formalism and electrostatics", Integrated Systems Laboratory, ETH Zurich (2012), 34 pages.
Kim, Kyoung-Youm and Lee, Byoungho, "Quantum transport modeling in anisotropic semiconductors using Wigner function formulation", Proceedings Conference on Optoelectronic and Microelectronic Materials and Devices, COMMAD 2000. (2000), pp. 4.
Arovas, Daniel "Lecture Notes on Condensed Matter Physics, Chapter 1 Boltzmann Transport", Department of Physics, University of California, San Diego (2010), pp. 46.
Grau-Crespo, R. "Electronic structure and magnetic coupling in FeSbO4: A DFT study using hybrid functionals and GGA+U methods", Physical Review B 73, (2006), pp. 9.
Muramatsu, A., "Quantum Monte Carlo for lattice fermions", in: M.P. Nightingale, C.J. Umriga (Eds.), Proceedings of the NATO Advanced Study Institute on Quantum Monte Carlo Methods in Physics and Chemistry, Kluwer Academic Publishers, (1999), pp. 32.
Gross, E.K.U. and Maitra, N.T., "Introduction to TDDFT", Chapter in Fundamentals of Time-Dependent Density Functional Theory, Springer-Verlag (2012), 58 pages.
Marques, M.A.L. and Gross, E.K.U., "Time-dependent density functional theory," C. Fiolhais, F. Nogueira, M.A.L. Marques (Eds.), A Primer in Density Functional Theory, Springer Lecture Notes in Physics, vol. 620, Springer (2003), pp. 144-184.
Ryndyk, D.A., "Tight-binding model", Lectures 2006-2007, Dresden University of Technology, (2006-2007), pp. 26-30.
Bank, R.E., "Numerical Methods for Semiconductor Device Simulation", IEEE Transactions on Electron Devices, vol. ED-30, No. 9, (1983), pp. 1031-1041.
Lee, J.F., "Time-Domain Finite-Element Methods", IEEE Transactions on Antenna and Propagation, vol. 45, No. 3, (1997), pp. 430-442.
Eymard, R., "Finite Volume Methods", course at the University of Wroclaw, (2008), manuscript update of the preprint "n0 97-19 du LATP, UMR 6632, Marseille, (Sep. 1997)," Handbook of Numerical Anaylsis P.G. Ciarlet, J.L. Lions, eds. vol. 7, pp. 713-1020.
Chen, X.L., "An advanced 3D boundary element method for characterizations of composite materials", Engineering Analysis with Boundary Elements 29, (2005), pp. 513-523.
Marx, D., "Ab initio molecular dynamics: Theory and Implementation", Modern Methods and Algorithms of Quantum Chemistry, J. Grotendorst (Ed.), John von Neumann Institute for Computing, Julich, NIC Series, vol. 1, (2000), pp. 150.
Kresse, Georg, et al., "VASP the Guide",http://cms_mpi.univie.ac.atNASP, Sep. 9, 2013, Vienna, Austria, pp. 1-203.
PCT/US2014/057707—International Search Report and Wirtten Opinion dated Dec. 29, 2014, 16 pages.
PCT/US2014/057707—International Preliminary report on Patentability, 8 pages.
PCT/US2014/057637—International Preliminary Report on Patentability dated Mar. 29, 2016, 7 pages.
PCT/US2014/057840—International Search Report dated Nov. 28, 2014, 9 pages.
U.S. Appl. No. 15/081,735—Office Action dated Jun. 15, 2016, 16 pages.
Saha et al., Technology CAD: Technology Modeling, Device Design and Simulation, 2004 VLSI Design Tutorial, Mubai, India, Jan. 5, 2004, 227 pages.
U.S. Appl. No. 14/497,681—Office Action dated Aug. 25, 2016, 20 pages.
Ayyadi et al., Semiconductor Simulations Using a Coupled Quantum Drift-Diffusion Schrodinger-Poisson Model, Aug. 12, 2004, Vienna University of Technology, pp. 1-19.
Kresse et al., VASP the Guide (Sep. 9, 2013), pp. 203.
CN 201680070832.8—Request for Exam and Voluntary Amendments filed Oct. 30, 2018, 39 pages.
EP 16860917.0—Voluntary Amendments, dated Feb. 27, 2019, 8 pages.

* cited by examiner

| k-sampling | Energy (eV/atom) | Force (eV/Å) | Time (sec) |
|---|---|---|---|
| 1x1x1 | -3.11 | -4.04 | 1.3 |
| 2x2x2 | -4.32 | -3.93 | 2.9 |
| 3x3x3 | -4.39 | -3.90 | 10.0 |
| 4x4x4 | -4.40 | -3.90 | 22.4 |
| 5x5x5 | -4.40 | -3.90 | 45.7 |

ATOMIC STRUCTURE OPTIMIZATION

CROSS-REFERENCE TO OTHER APPLICATIONS

This application is a Continuation-in-Part of U.S. patent application Ser. No. 14/928,615, entitled "ATOMIC STRUCTURE OPTIMIZATION," filed Oct. 30, 2015, which application is incorporated herein by reference in its entirety.

FIELD OF THE INVENTION

The present invention relates to a computer system provided with a control module for controlling ab initio atomic structure modules for simulating the behavior of structures and materials at multiple scales with different modules, for purposes of evaluating such structures and materials for use in integrated circuit devices.

BACKGROUND

As device dimensions shrink, device designers are turning to materials other than silicon, such as III-V semiconductor alloys. Silicon has been used for decades and is well-understood, but the behavior of these new materials is yet to be fully characterized.

Properties of materials can be calculated from ab initio, or first principles, calculations of electronic structures based on quantum physics theories. First principles models can be used to compute thermodynamic and transport properties of pure materials, defects and dopants. Results of first principles calculations are used to drive higher-level calculations, such as kinetic Monte Carlo and continuum calculations. From these, device properties are derived. In order to model the materials, first principles calculations are used to determine fundamental material properties, such as the equilibrium atomic structures and their energies of materials under evaluation. Such fundamental material properties include such quantities as the defect structure and a migration path of the defect, the atomic forces of the atomic structure, positions of one or more atoms of the atomic structure, atomic coordinates of constituent atoms in a unit cell of the atomic structure, the minimum energy of a unit cell of the atomic structure, formation energy of defects, migration energy of defects, entropy of defect formation, entropy of defect migration, defect concentration, defect diffusivity, and so on.

Performing first principles calculations is difficult and costly. Existing methods for structure optimization suffer from slow convergence and occasional incorrect solutions. To solve the issues, laborious human intervention for analysis and tweaking often are required case-by-case. Such intervention can require in-depth understanding of quantum physics and related theories, and can take a person significant amount of time to understand the calculations. Also, it can require manual work to extract physical parameters from results of the first principles calculations. If not done correctly, the ab initio calculation can become stuck in a saddle point of the iteration, or require enormous amounts of time to converge. Alternatively, if done at too large a granularity, the calculation can result in low accuracy.

It is desirable to provide a computer system with a control module that can optimize utilization of the computing resources, while at the same time automatically sidestepping local optima to guide the calculations toward global optima at high accuracy. Such a computer system can determine the basic properties of new or previously uncharacterized materials, thereby greatly improving both the computer system and the technology for evaluating new materials for use in future integrated circuit devices or their manufacture.

SUMMARY

One aspect is a system comprising an EDA tool transforming a model of an atomic structure into a final state to determine a plurality of ab initio characteristics of the atomic structure. The system comprises a control module causing a plurality of ab initio atomic structure relaxation modules to iteratively transform the model of the atomic structure to determine the plurality of ab initio characteristics of the atomic structure. The plurality of ab initio atomic structure relaxation modules controlled by the control module includes:
  a first ab initio atomic structure relaxation module responsive to the control module by transforming the model of the atomic structure into an intermediate state of the model of the atomic structure, based on a conjugate gradient minimization; and
  a second ab initio atomic structure relaxation module responsive to the control module by transforming the intermediate state of the model of the atomic structure into the final state of the model of the atomic structure, based on a quasi-Newton minimization.

Another aspect is a computer executed method of transforming a model of an atomic structure into a final state to determine a plurality of ab initio characteristics of the atomic structure, comprising:
  the computer causing a plurality of ab initio atomic structure relaxation modules to iteratively transform the model of the atomic structure to determine the plurality of ab initio characteristics of the atomic structure, including:
    the computer causing a first ab initio atomic structure relaxation module to transform the model of the atomic structure into an intermediate state of the model of the atomic structure, based on a conjugate gradient minimization; and
    the computer causing a second ab initio atomic structure relaxation module to transform the intermediate state of the model of the atomic structure into the final state of the model of the atomic structure, based on a quasi-Newton minimization.

In various embodiments, an iterative transformation of any of the plurality of ab initio atomic structure relaxation modules yields atomic forces of constituent atoms in a unit cell of the atomic structure.

In various embodiments, different iterative transformations of the plurality of ab initio atomic structure relaxation modules change one or more positions of one or more atoms of the atomic structure as inputs.

In various embodiments, the plurality of ab initio characteristics of the atomic structure includes a plurality of atomic coordinates of constituent atoms in a unit cell of the atomic structure.

In various embodiments, the plurality of ab initio characteristics of the atomic structure includes a minimum energy of a unit cell of the atomic structure.

In various embodiments, the intermediate state of the model of the atomic structure and the final state of the model of the atomic structure inform ab initio characteristics including any of formation energy of defects, migration energy of defects, entropy of defect formation, entropy of defect migration, defect concentration, and defect diffusivity.

Another aspect is a system comprising an EDA tool transforming a model of an atomic structure into a final state to determine a plurality of ab initio characteristics of the atomic structure. The system comprises a control module causing a set of one or more ab initio modules to perform a plurality of iterative transformations to determine the plurality of ab initio characteristics of an atomic structure. The plurality of iterative transformations includes:

a first iterative transformation with a first k-mesh resolution having any of a single gamma point in a Brillouin zone of the atomic structure and a 2×2×2 k-mesh in the Brillouin zone of the atomic structure, the first iterative transformation responsive to the control module by transforming the model of the atomic structure into an intermediate state of the model of the atomic structure; and a second iterative transformation with a second k-mesh resolution, the second k-mesh resolution being higher than the first k-mesh resolution, the second iterative transformation using as input atomic coordinates of a supercell from the first iterative transformation, the second iterative transformation responsive to the control module by transforming the intermediate state of the model of the atomic structure into the final state of the model of the atomic structure.

Another aspect is a computer executed method of transforming a model of an atomic structure into a final state to determine a plurality of ab initio characteristics of the atomic structure, comprising:

the computer causing a set of one or more ab initio modules to perform a plurality of iterative transformations to determine the plurality of ab initio characteristics of an atomic structure, including:

the computer causing a first iterative transformation with a first k-mesh resolution having any of a single gamma point in a Brillouin zone of the atomic structure and a 2×2×2 k-mesh in the Brillouin zone of the atomic structure, the first iterative transformation responsive to the control module by transforming the model of the atomic structure into an intermediate state of the model of the atomic structure; and the computer causing a second iterative transformation with a second k-mesh resolution, the second k-mesh resolution being higher than the first k-mesh resolution, the second iterative transformation using as input atomic coordinates of a supercell from the first iterative transformation, the second iterative transformation responsive to the control module by transforming the intermediate state of the model of the atomic structure into the final state of the model of the atomic structure.

In various embodiments, the first k-mesh resolution is the single gamma point in the Brillouin zone.

In various embodiments, the first k-mesh resolution is the 2×2×2 k-mesh in the Brillouin zone In various embodiments, the first and the second iterative transformations are performed with a supercell having any of (i) at least 64 atoms and (ii) at least 63 atoms and a vacancy.

In various embodiments, the first and the second iterative transformations inform the plurality of ab initio characteristics including a defect structure and a migration path of the defect.

In various embodiments, an iterative transformation of any of the plurality of iterative transformations yields atomic forces of the atomic structure.

In various embodiments, different iterative transformations of the plurality of iterative transformations change one or more positions of one or more atoms of the atomic structure as inputs.

In various embodiments, the plurality of ab initio characteristics of the atomic structure includes a plurality of atomic coordinates of a plurality of constituent atoms in a unit cell of the atomic structure.

In various embodiments, the plurality of ab initio characteristics of the atomic structure includes a minimum energy of a unit cell of the atomic structure.

In various embodiments, the first and second sets of solutions inform the plurality of ab initio characteristics including any of formation energy of defects, migration energy of defects, entropy of defect formation, entropy of defect migration, defect concentration, and defect diffusivity.

One aspect is a computer-implemented apparatus comprising a computer with a control module causing a plurality of ab initio modules to iteratively perform ab initio simulation to determine a plurality of ab initio characteristics of an atomic structure, the plurality of ab initio atomic structure relaxation modules controlled by the control module including:

a first ab initio atomic structure relaxation module based on a conjugate gradient minimization; and a second ab initio module based on a quasi-Newton minimization.

The control module causes: (i) the first ab initio module to determine a first set of solutions, and then (ii) based on the first set of solutions, a subsequent ab initio simulation including the second ab initio module to determine a second set of solutions.

In one embodiment an iterative transformation of any of the plurality of ab initio atomic structure relaxation modules yields atomic forces of the atomic structure.

In one embodiment different iterative transformations of the plurality of ab initio atomic structure relaxation modules change one or more positions of one or more atoms of the atomic structure as inputs.

In one embodiment the plurality of ab initio characteristics of the atomic structure includes a plurality of atomic coordinates of a plurality of constituent atoms in a unit cell of the atomic structure.

In one embodiment the plurality of ab initio characteristics of the atomic structure includes a minimum energy of a unit cell of the atomic structure.

In one embodiment the first and second sets of solutions inform ab initio characteristics including any of formation energy of defects, migration energy of defects, entropy of defect formation, entropy of defect migration, defect concentration, and defect diffusivity.

Another aspect is a computer-implemented apparatus comprising:

a computer with a control module causing a set of one or more ab initio modules to perform a plurality of iterative transformations of ab initio simulation to determine a plurality of ab initio simulation characteristics of an atomic structure, the plurality of iterative transformations including:

a first iterative transformation of ab initio simulation with a first k-mesh resolution having any of a single gamma point in a Brillouin zone of the atomic structure and a 2×2×2 k-mesh in the Brillouin zone of the atomic structure; and a second iterative transformation of ab initio simulation with a second k-mesh resolution, the second k-mesh resolution being higher than the first k-mesh resolution, the second iterative transformation using as input atomic coordinates of a supercell from the first iterative transformation.

The control module causes: (i) the first iterative transformation of ab initio simulation to determine a first set of solutions to the plurality of ab initio simulation characteristics of the atomic structure, and then (ii) the second iterative transformation of ab initio simulation to determine a second set of solutions to the plurality of ab initio simulation characteristics of the atomic structure.

In one embodiment the first k-mesh resolution is single gamma point in the Brillouin zone.

In one embodiment the first k-mesh resolution is the 2×2×2 k-mesh in the Brillouin zone.

In one embodiment the first and the second iterative transformations of the ab initio simulation are performed with a supercell having at least 64 atoms for defect-free pristine supercell and 63 atoms for supercell with a vacancy.

In one embodiment the first and the second iterative transformations of the ab initio simulation inform ab initio simulation characteristics including a defect structure and a migration path of a defect.

In one embodiment an iterative transformation of any of the plurality of iterative transformations of ab initio simulation yields atomic forces of the atomic structure.

In one embodiment different iterative transformations of the plurality of iterative transformations of ab initio simulation change one or more positions of one or more atoms of the atomic structure as inputs.

In one embodiment the plurality of ab initio simulation characteristics of the atomic structure includes a plurality of atomic coordinates of a plurality of constituent atoms in a unit cell of the atomic structure.

In one embodiment the plurality of ab initio simulation characteristics of the atomic structure includes a minimum energy of a unit cell of the atomic structure.

In one embodiment the first and second sets of solutions inform ab initio simulation characteristics including any of formation energy of defects, migration energy of defects, entropy of defect formation, entropy of defect migration, defect concentration, and defect diffusivity.

Another aspect of the technology are computer readable medium having stored thereon in a non-transitory manner, software code executable by a computer, the software code comprising a control module as described herein.

Another aspect of the technology is a computer executed method with a control module as described herein.

Various embodiments are disclosed herein.

Other aspects and advantages of the present technology can be seen on review of the drawings, the detailed description and the claims, which follow.

DETAILED DESCRIPTION

A detailed description of embodiments of the present invention is provided with reference to the Figures.

Figure 1:
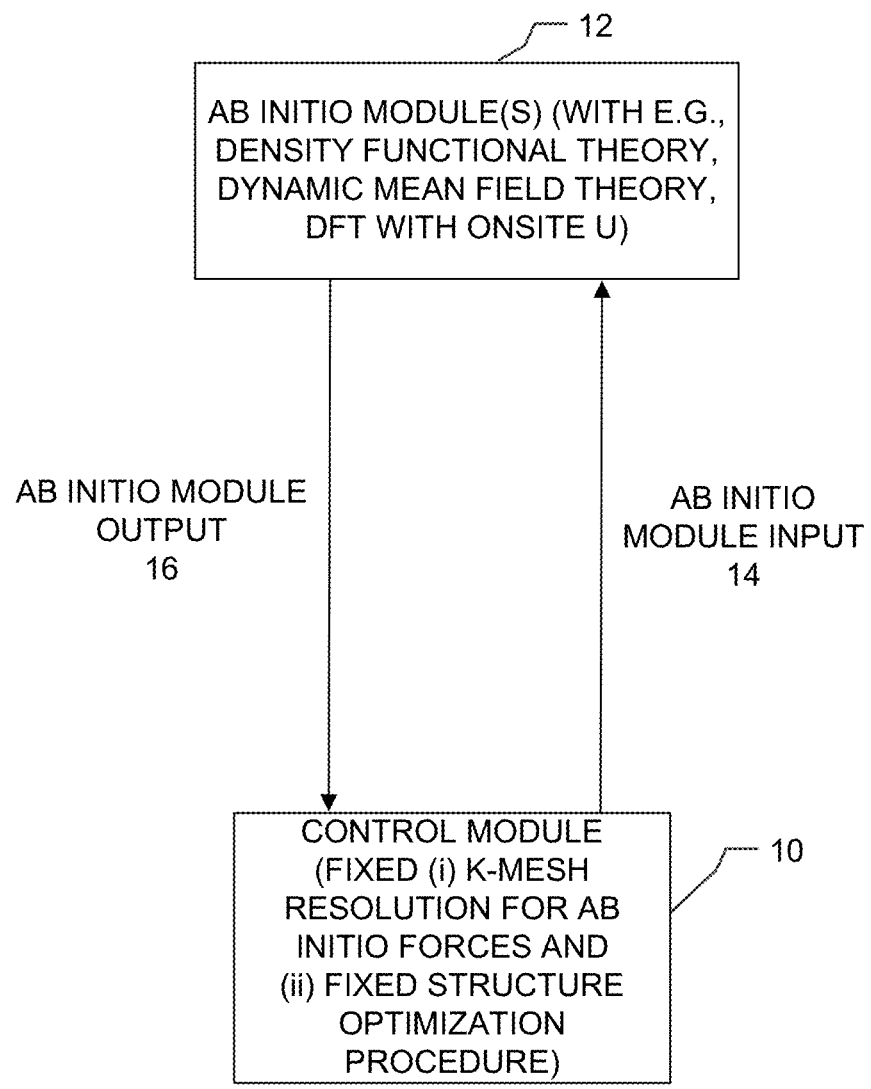
FIG. 1 is a block diagram of a control module in communication with one or more ab initio modules, with fixed parameters or other configuration.

FIG. 1 is a block diagram of a control module 10 in communication with one or more ab initio modules 12.

Ab initio module input 14 is sent from control module 10 to ab initio module 12. Ab initio module output 16 is sent back from ab initio module 12 to control module 10.

In FIG. 1, control module 10 instructs ab initio module 12 to perform ab initio simulation with a fixed k-mesh resolution and a fixed ab initio module, such as only conjugate gradient or only quasi-Newton.

FIGS. 2-5 are illustrative process flows that show unfavorable outcomes with the system of FIG. 1.

Figure 2:
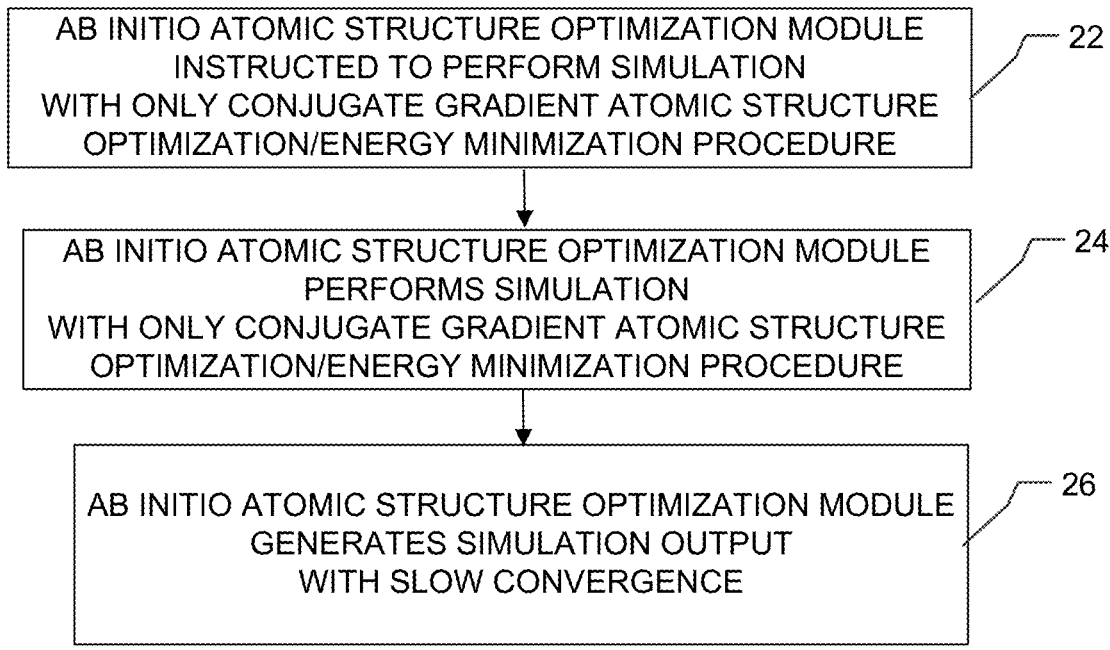
FIGS. 2, 3, 4, and 5 are illustrative process flows that show unfavorable outcomes with the system of FIG. 1.

In FIG. 2, at 22 control module 10 instructs ab initio module 12 to perform ab initio simulation with a fixed ab initio module, such as only conjugate gradient. At 24, accordingly ab initio module 12 performs ab initio simulation with only conjugate gradient as the ab initio module. Accordingly, at 26, ab initio module 12 generates ab initio simulation output with high computational cost.

Figure 3:
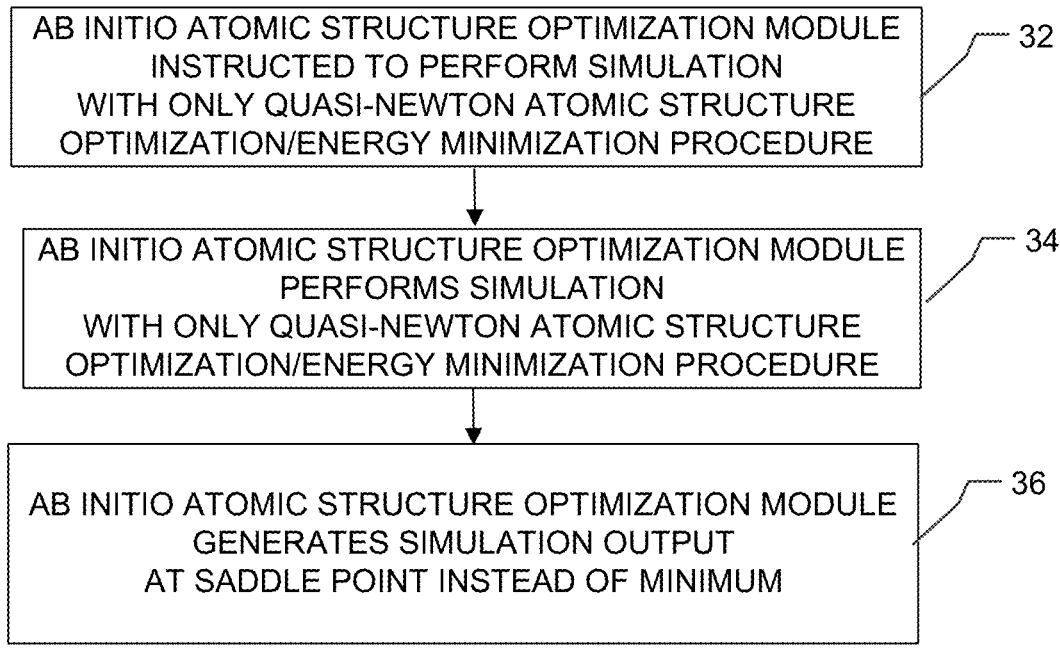

In FIG. 3, at 32 control module 10 instructs ab initio module 12 to perform ab initio simulation with a fixed ab initio module, such as only quasi-Newton. At 34, accordingly ab initio module 12 performs ab initio simulation with only quasi-Newton as the ab initio module. Accordingly, at 36, ab initio module 12 generates ab initio simulation output as a saddle point instead of a true minimum.

Figure 4:
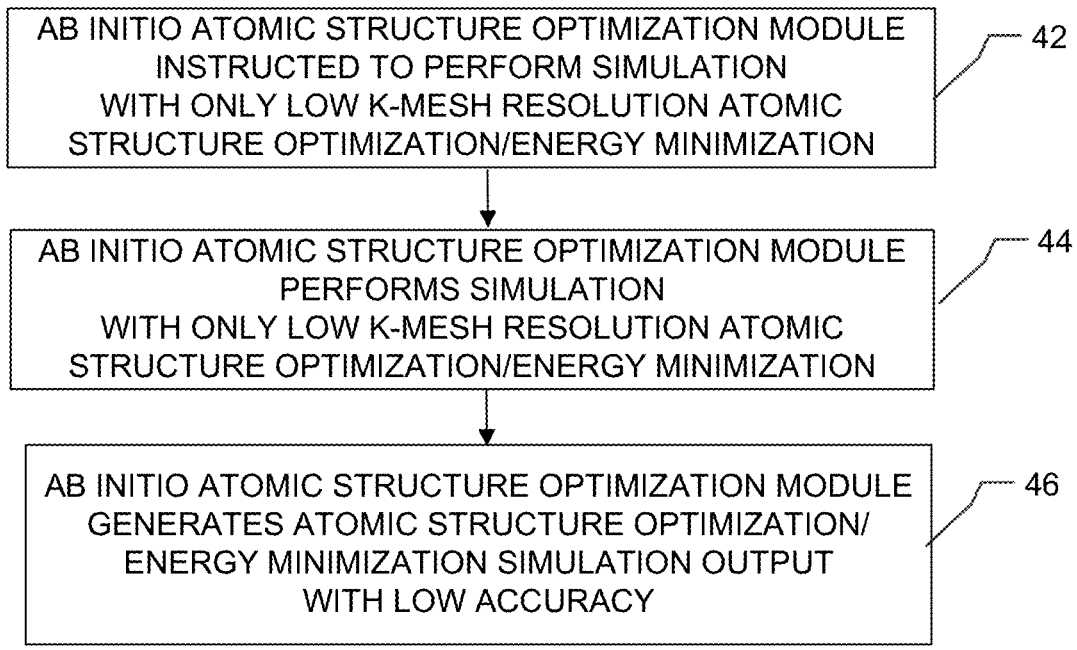

In FIG. 4, at 42 control module 10 instructs ab initio module 12 to perform ab initio simulation with only a low k-mesh resolution. At 44, accordingly ab initio module 12 performs ab initio simulation with only the low k-mesh resolution. Accordingly, at 46, ab initio module 12 generates ab initio simulation output with low accuracy.

Figure 5:
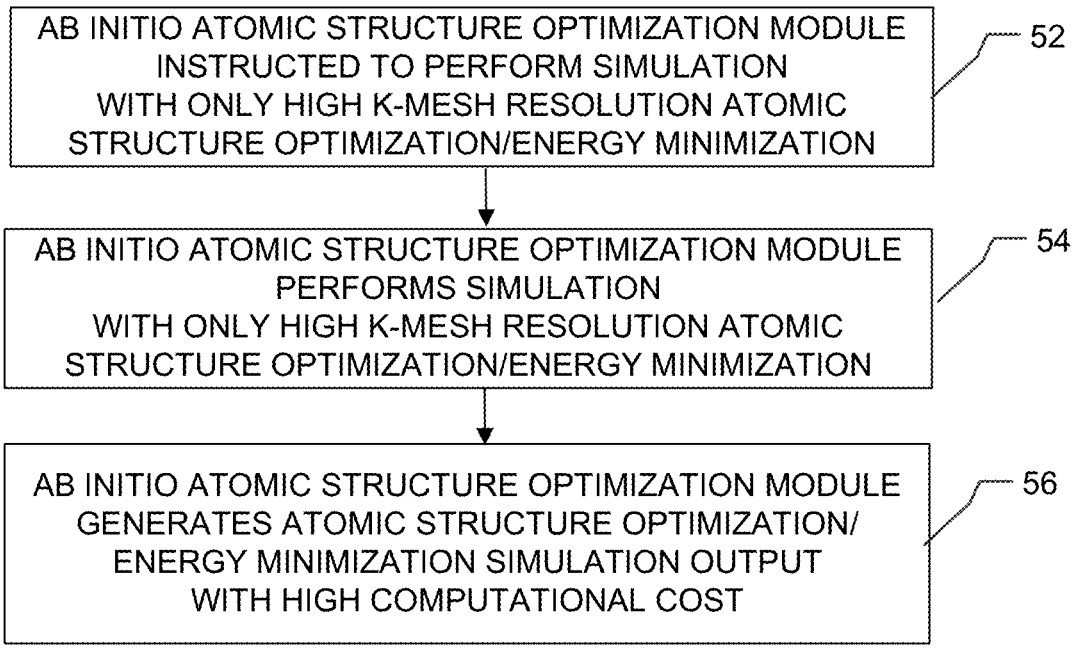

In FIG. 5, at 52 control module 10 instructs ab initio module 12 to perform ab initio simulation with only a high k-mesh resolution. At 54, accordingly ab initio module 12 performs ab initio simulation with only the high k-mesh resolution. Accordingly, at 56, ab initio module 12 generates ab initio simulation output with high computational cost.

Figure 6:
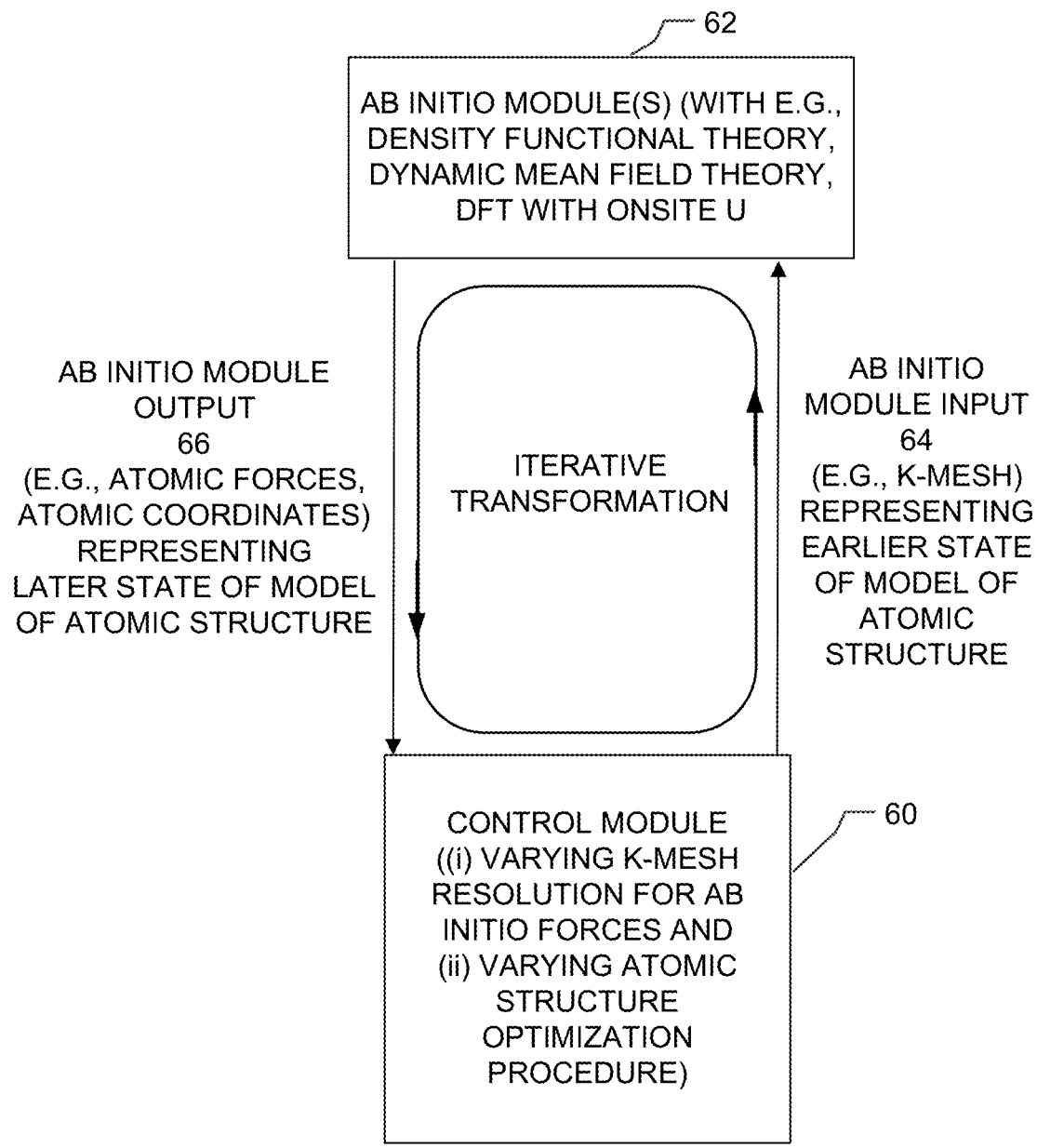
FIG. 6 is a block diagram of a control module in communication with one or more ab initio modules, with parameters or other configuration varying across iterative transformations.

FIG. 6 is a block diagram of a control module 60 in communication with one or more ab initio modules 62. Control module 60 can be integrated into, or in turn be in communication with a multi-scale modeler, for example, Synopsys Sentaurus Device and/or Synopsys Sentaurus Process. Ab initio module 62 can be, for example, VASP, MedeA, ATK, Materials Studio, QuantumEspresso, and/or ABINIT. "Ab initio" or "first principles" approaches require minimal empirical input to generate accurate ground state total energies for arbitrary configurations of atoms. Such approaches make use of the fundamental governing quantum mechanical equations, and require very little in the way of externally-supplied materials parameters. This capability makes these methods well-suited to investigate new materials and provide detailed physical insight into materials properties and processes. However "ab initio" modules also are extremely computation intensive. As used herein, an "ab initio" or "first principles" analysis approach or module is an approach or module that develops its results at least in part by solving Schrödinger's equation based on positions and types of atoms. Other example first principles approaches that can be used herein include EPM (Empirical Pseudopotential Method) tools, and ETB (Empirical Tight Binding) tools, and combinations of approaches.

Ab initio module input 64 is sent from control module 60 to ab initio module 62 and includes atomic structure, shown by atomic coordinates or vectors of all constituent atoms in a unit cell, and shape and size of the unit cell. The ab initio module input 64 represents an earlier state of the model of atomic structure. Different iterative transformations can vary one or more positions of the one or more atoms.

Ab initio module output 66 is sent back from ab initio module 62 to control module 60 and includes any of equilibrium atomic structure equilibrium atomic energy, formation energy of defects, defect concentration, and Hellman-Feynman forces. The ab initio module output 66 represents a later state of the model of atomic structure. As the different iterative transformations vary one or more positions of the one or more atoms, comparison of the different results indicates which of the input atomic structures has the equilibrium structure.

In FIG. 6, control module 60 iteratively instructs ab initio module 62 to perform iterative transformations of the model of atomic structure with varying k-mesh resolution of the Brillouin zone and/or varying ab initio module, such as both conjugate gradient and quasi-Newton.

Figure 7:
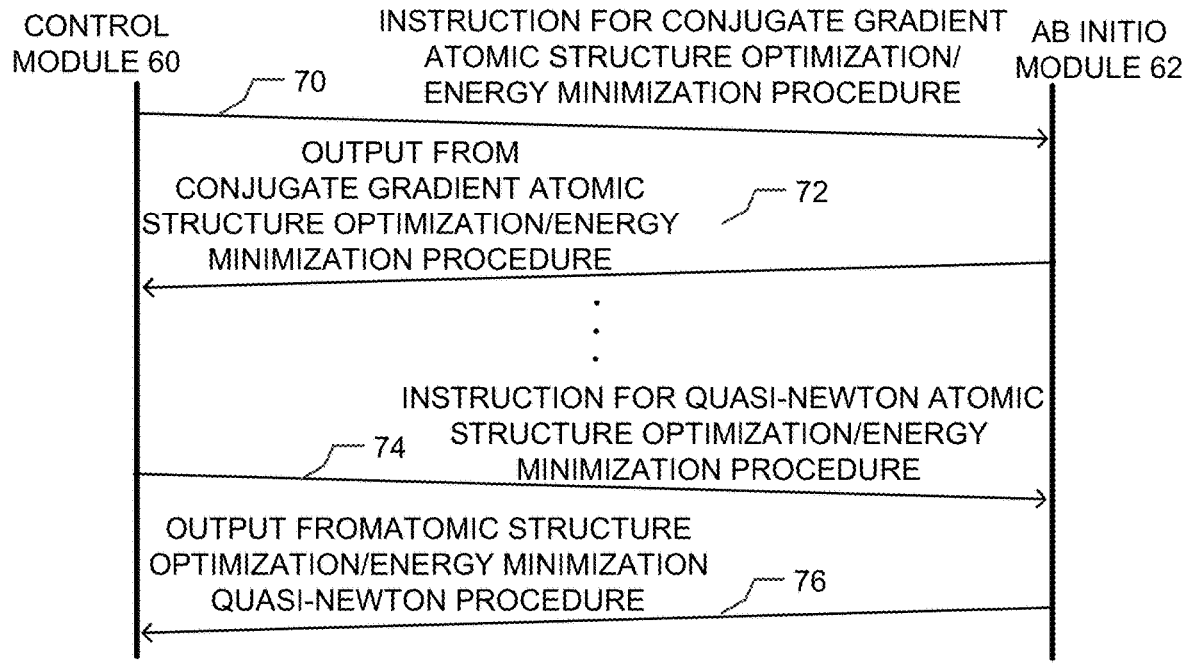
FIGS. 7 and 8 are example ab initio iterative transformations by the ab initio system of FIG. 6.
Figure 8:
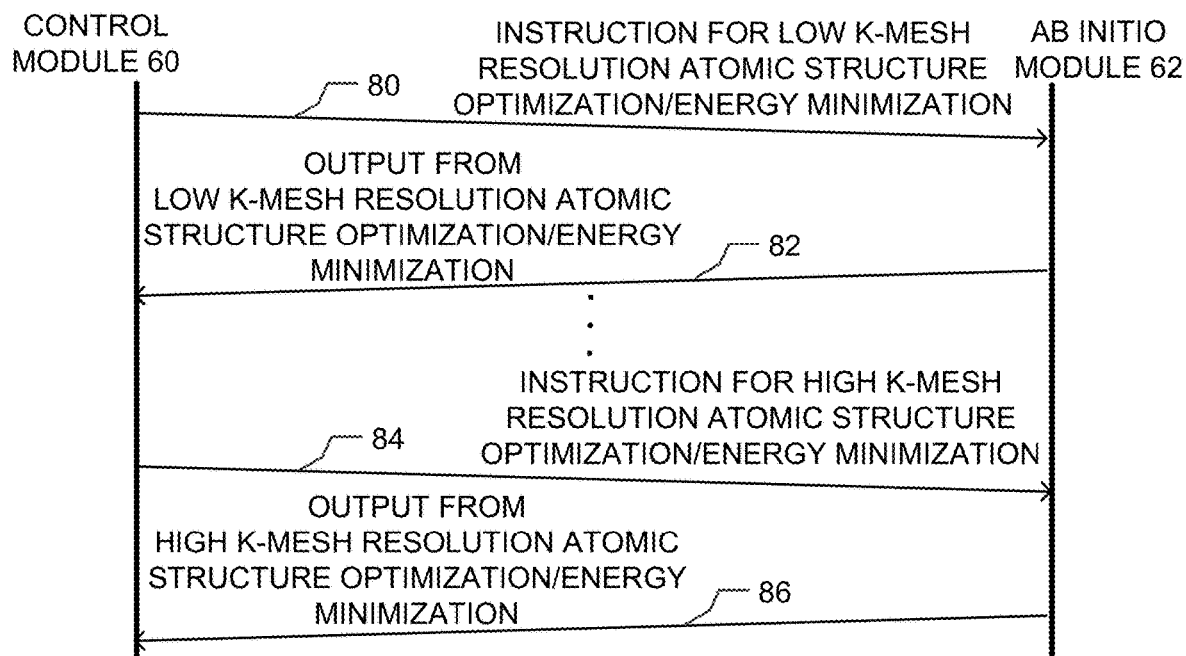

FIGS. 7-8 are example ab initio iterative transformations by the system of FIG. 6. FIGS. 7 and 8 demonstrate how different iterative transformations change significant parameters or other characteristics of the ab initio iterative transformations which remain constant in the example ab initio simulations of FIGS. 2-5.

In FIG. 7, with an earlier iterative transformation at 70 control module 60 instructs ab initio module 62 to perform ab initio iterative transformation with a first ab initio module, such as conjugate gradient. Examples of conjugate gradient minimization include any of Fletcher-Reeves, Davison-Fletcher-Powell, Polak-Ribiere, and Broyden-Fletcher-Goldfarb-Shanno. At 72, accordingly ab initio module 62 performs ab initio iterative transformation with conjugate gradient as the ab initio module. Because the ab initio iterative transformation uses conjugate gradient instead of quasi-Newton in an earlier iterative transformation, the results avoid any saddle points which are thermodynamically unstable and are irrelevant to equilibrium properties.

With a later iterative transformation at 74, control module 60 instructs ab initio module 62 to perform ab initio iterative transformation with a second ab initio module, such as quasi-Newton. Another example of quasi-Newton is pseudo-Newton-Raphson minimization. At 76, accordingly ab initio module 62 performs ab initio iterative transformation with quasi-Newton as the ab initio module. Because the ab initio iterative transformation uses quasi-Newton instead of conjugate gradient in a later iterative transformation, the results avoid high computational cost. Near a local minimum where the potential energy surface can be approximated by a quadratic function, quasi-Newton works much more efficiently, and quickly finds the solution.

In FIG. 8, with an earlier iterative transformation at 80 control module 60 instructs ab initio module 62 to perform ab initio iterative transformation with a low k-mesh resolution. An example of a low k-mesh resolution is a single gamma point in a Brillouin zone, at the vector k=<0, 0, 0>. Another example of a low k-mesh resolution is a 2×2×2 k-mesh in a Brillouin zone. At 82, accordingly ab initio module 62 performs ab initio iterative transformation with the low k-mesh resolution. Because the ab initio iterative transformation uses the low k-mesh resolution in an earlier iterative transformation, the results avoid high computational cost.

With a later iterative transformation at 84, control module 60 instructs ab initio module 62 to perform ab initio iterative transformation with a high k-mesh resolution. At 86, accordingly ab initio module 62 performs ab initio iterative transformation with the high k-mesh resolution. Because the ab initio iterative transformation uses the high k-mesh resolution in a later iterative transformation, the results are highly accurate.

In some embodiments the earlier and the later iterative transformations of the ab initio iterative transformations are performed with a supercell having at least 64 atoms for defect-free pristine supercell and 63 atoms for supercell with a vacancy. A supercell having 63 or less atoms (62 or less atoms for supercell with a vacancy) can fail to isolate defects of the supercell or boundary condition interaction between copies of the supercell. Generally larger supercells are superior iterative transformations, though at great computational cost.

In another embodiment, aspects of FIGS. 7 and 8 can be combined. For example, an earlier iterative transformation can use both conjugate gradient and a low k-mesh resolution, and a later iterative transformation can use both quasi-Newton and a high k-mesh resolution.

In another example, an earlier iterative transformation can use both conjugate gradient and a later iterative transformation can use quasi-Newton. Both the earlier iterative transformation and the later iterative transformation use the same k-mesh resolution.

In another example, an earlier iterative transformation can use a low k-mesh resolution and a later iterative transformation can use a high k-mesh resolution. Both the earlier iterative transformation and the later iterative transformation use the same ab initio module, such as conjugate gradient or quasi-Newton.

Figures 9, 10:
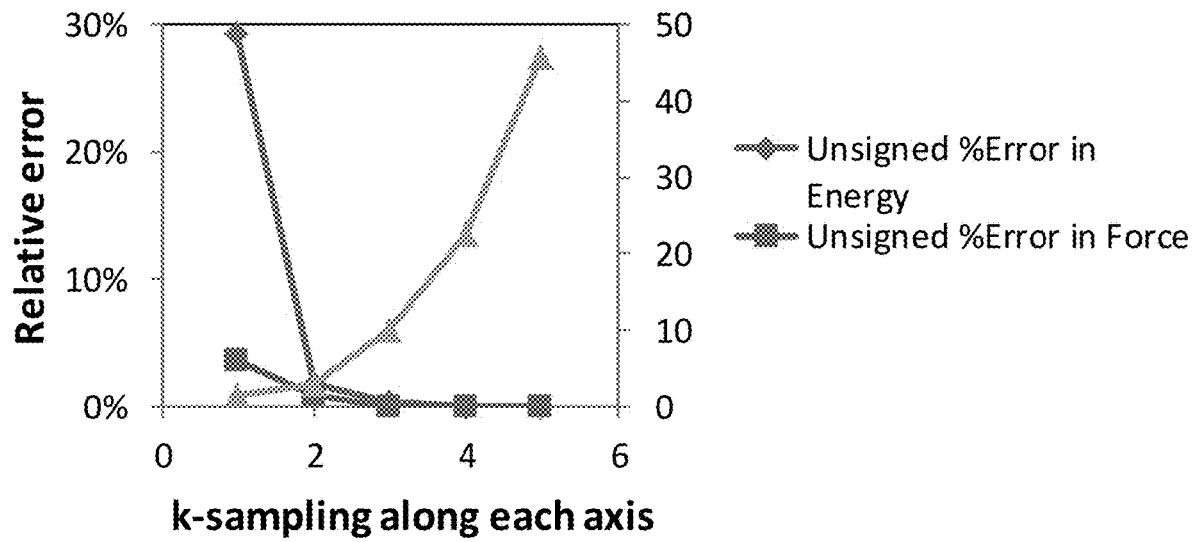
FIG. 9 is a graph of relative error and timing versus k-sampling resolution.
FIG. 10 is a table showing the fast convergence of energy and force for different k-sampling resolutions.

FIG. 9 is a graph of relative error and timing versus k-sampling resolution. FIG. 9 shows how lower-resolution k-sampling for the k-mesh results in faster iterative transformation and less error than higher-resolution k-sampling for the k-mesh. For example, 1×1×1 k-sampling is 17 times faster than 4×4×4 k-sampling.

FIG. 10 is a table showing the fast convergence of energy and force for different k-sampling resolutions, in particular for the case of 8-atom GaAs cubic cell, where one Ga atom is displaced by 0.03 angstrom from its equilibrium position toward As to generate non-zero forces. Even with low resolution gamma-only 1×1×1 k-sampling, the force error is 0.14 eV per angstrom, or 3.6% error relative to high resolution 4×4×4 k-sampling which gives fully converged energy below 0.01 eV/atom and forces below 0.01 eV per angstrom. This translates into a 0.001 angstrom deviation of the position from equilibrium, which is more than sufficient for pre-optimization. Loss of accuracy in forces is minimal, as full-resolution sampling is used in real-space.

In one embodiment, an early phase of pre-optimization uses 1×1×1 k-sampling and relaxes the structure until the energy change between two moves is smaller than 0.01 eV. Another phase continues from the pre-optimized structure of the early phase using 2×2×2 k-sampling until the energy change is below 0.005 eV. The 2×2×2 k-sampling gives much more accurate forces: deviation is less than 0.03 eV/A or 0.8%. These two pre-optimization steps move the structure very close to its minimum. Final optimization with full-resolution k-sampling quickly finds the minimum.

In one example with an interstitial at 001 Ga in 64-atom 2×2×2 unit cell, the ab initio iterative transformation of FIG. 6 is 6 times faster than FIG. 1. A minority of the time is spent on pre-optimization, and the bulk of the time is spent on refining the pre-optimization.

The ab initio iterative transformation of FIG. 6 is robust, in that out of 17 different defects of InGaAs, all 17 different defects converge. Using the conjugate gradient module with the ab initio iterative transformation of FIG. 1, 5 structures of the 17 different structures fail to even converge, let alone finish with a reasonable amount of computation.

Figure 11:
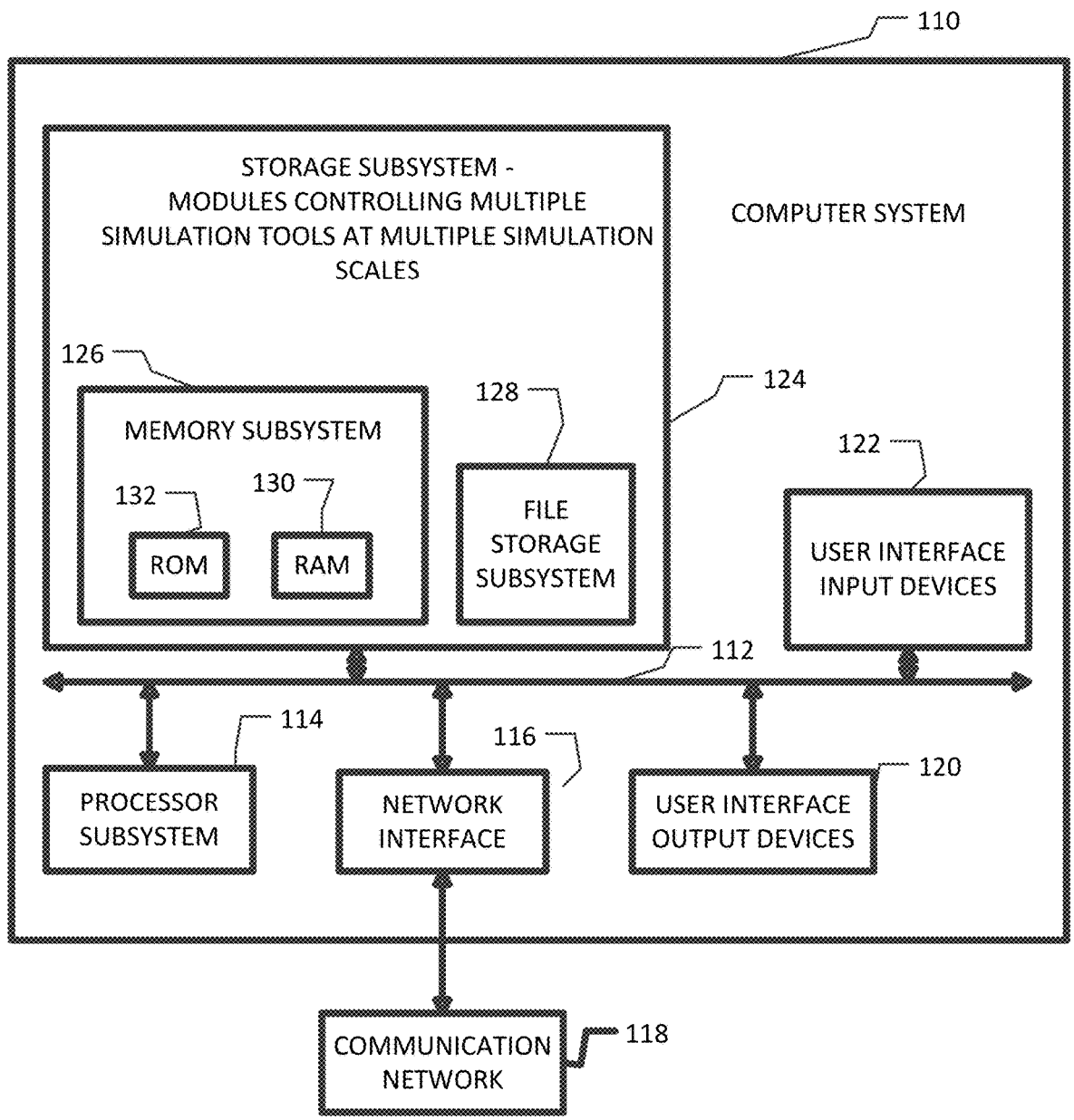
FIG. 11 is a simplified block diagram of a computer system configured to control ab initio iterative transformation.

FIG. 11 is a simplified block diagram of a computer system configured to control ab initio iterative transformation to implement any of the methods and processes herein.

Computer system 110 typically includes a processor subsystem 114 which communicates with a number of peripheral devices via bus subsystem 112. These peripheral devices may include a storage subsystem 124, comprising a memory subsystem 126 and a file storage subsystem 128, user interface input devices 122, user interface output devices 120, and a network interface subsystem 116. The storage subsystem 128 includes non-transitory memory storing computer programs, and resources to configure the data processing systems as an EDA tool for controlling multiple iterative transformation tools at multiple scales as described herein. The tool can include an API configured to use input parameter sets, and to use the modules of the tool using the input parameter sets. The tool can comprise a data processor and storage configured to provide computer program instructions of the tool. Alternatively, the tool can comprise software modules on a computer readable medium in a nonvolatile manner.

The input and output devices allow user interaction with computer system 110. Network interface subsystem 116 provides an interface to outside networks, including an interface to communication network 118, and is coupled via communication network 118 to corresponding interface devices in other computer systems. Communication network 118 may comprise many interconnected computer systems and communication links. These communication links may be wireline links, optical links, wireless links, or any other mechanisms for communication of information, but typically it is an IP-based communication network. While in one embodiment, communication network 118 is the Internet, in other embodiments, communication network 118 may be any suitable computer network.

The physical hardware component of network interfaces are sometimes referred to as network interface cards (NICs), although they need not be in the form of cards: for instance they could be in the form of integrated circuits (ICs) and connectors fitted directly onto a motherboard, or in the form of macrocells fabricated on a single integrated circuit chip with other components of the computer system.

User interface input devices 122 may include a keyboard, pointing devices such as a mouse, trackball, touchpad, or graphics tablet, a scanner, a touch screen incorporated into the display, audio input devices such as voice recognition systems, microphones, and other types of input devices. In general, use of the term "input device" is intended to include all possible types of devices and ways to input information into computer system 110 or onto computer network 118.

User interface output devices 120 may include a display subsystem, a printer, a fax machine, or non visual displays such as audio output devices. The display subsystem may include a cathode ray tube (CRT), a flat panel device such as a liquid crystal display (LCD), a projection device, or some other mechanism for creating a visible image. The display subsystem may also provide non visual display such as via audio output devices. In general, use of the term "output device" is intended to include all possible types of devices and ways to output information from computer system 110 to the user or to another machine or computer system.

Storage subsystem 124 stores the basic programming and data constructs that provide the functionality of certain embodiments. For example, the various modules implementing the functionality of certain embodiments may be stored in storage subsystem 124. These software modules are generally executed by processor subsystem 114.

Memory subsystem 126 typically includes a number of memories including a main random access memory (RAM) 130 for storage of instructions and data during program execution and a read only memory (ROM) 132 in which fixed instructions are stored. File storage subsystem 128 provides persistent storage for program and data files, and may include a hard disk drive, a floppy disk drive along with associated removable media, a CD ROM drive, an optical drive, or removable media cartridges. The databases and modules implementing the functionality of certain embodiments of the invention may have been provided on a computer readable medium such as one or more CD-ROMs, and may be stored by file storage subsystem 128. The host memory 126 contains, among other things, computer instructions which, when executed by the processor subsystem 114, cause the computer system to operate or perform functions as described herein. As used herein, processes and software that are said to run in or on "the host" or "the computer", execute on the processor subsystem 114 in response to computer instructions and data in the host memory subsystem 126 including any other local or remote storage for such instructions and data.

Bus subsystem 112 provides a mechanism for letting the various components and subsystems of computer system 110 communicate with each other as intended. Although bus subsystem 112 is shown schematically as a single bus, alternative embodiments of the bus subsystem may use multiple busses.

Computer system 110 itself can be of varying types including a personal computer, a portable computer, a workstation, a computer terminal, a network computer, a television, a mainframe, a server farm, or any other data processing system or user device. Due to the ever changing nature of computers and networks, the description of computer system 110 is intended only as a specific example for purposes of illustrating the preferred embodiments of the present invention. Many other configurations of computer system 110 are possible having more or less components than the computer system.

In addition, while the present invention has been described in the context of a fully functioning data processing system, those of ordinary skill in the art will appreciate that the processes herein are capable of being distributed in the form of a computer readable medium of instructions and data and that the invention applies equally regardless of the particular type of signal bearing media actually used to carry out the distribution. As used herein, a computer readable medium is one on which information can be stored and read by a computer system. Examples include a floppy disk, a hard disk drive, a RAM, a CD, a DVD, flash memory, a USB drive, and so on. The computer readable medium may store information in coded formats that are decoded for actual use in a particular data processing system. A single computer readable medium, as the term is used herein, may also include more than one physical item, such as a plurality of CD ROMs or a plurality of segments of RAM, or a combination of several different kinds of media. As used herein, the term does not include mere time varying signals in which the information is encoded in the way the signal varies over time.

Figure 12:
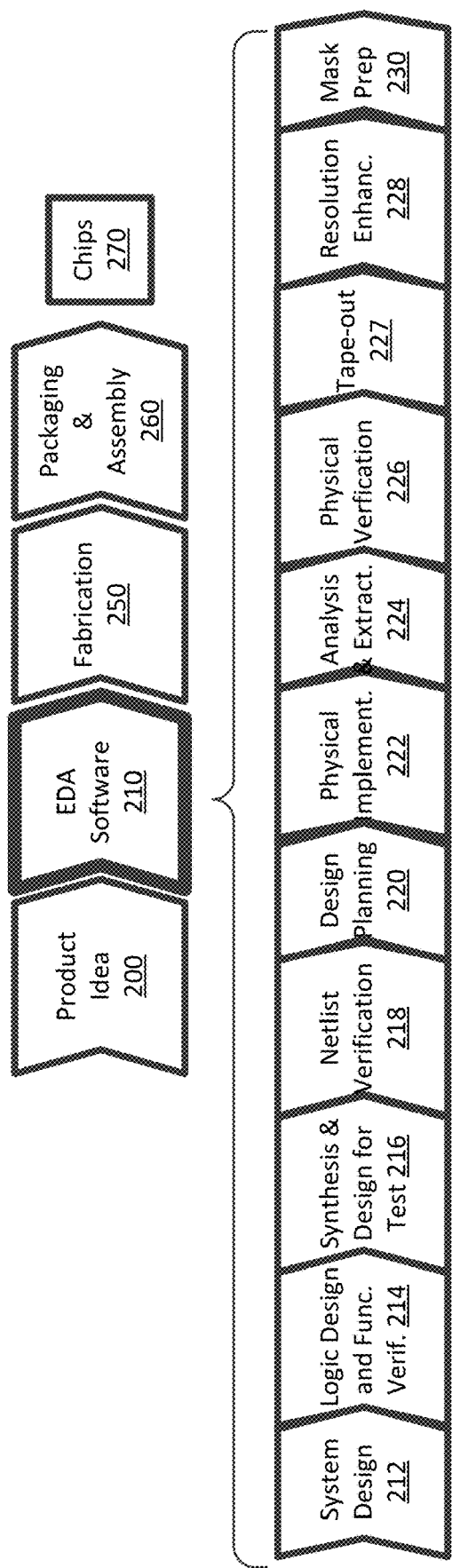
FIG. 12 illustrates EDA tools and process flow for integrated circuit design and manufacturing.

FIG. 12 illustrates EDA tools and process flow for integrated circuit design and manufacturing.

Aspects of the invention can be used to support an integrated circuit design flow. At a high level, the process starts with the product idea (step 200) and is realized in an EDA (Electronic Design Automation) software design process (step 210). When the design is finalized, it can be taped-out (step 227). At some point after tape out, the fabrication process (step 250) and packaging and assembly processes (step 260) occur resulting, ultimately, in finished integrated circuit chips (result 270).

The EDA software design process (step 210) is itself composed of a number of steps 212-230, shown in linear fashion for simplicity. In an actual integrated circuit design process, the particular design might have to go back through steps until certain tests are passed. Similarly, in any actual design process, these steps may occur in different orders and combinations. This description is therefore provided by way of context and general explanation rather than as a specific, or recommended, design flow for a particular integrated circuit.

A brief description of the component steps of the EDA software design process (step 210) will now be provided.

System design (step 212): The designers describe the functionality that they want to implement, they can perform what-if planning to refine functionality, check costs, etc. Hardware-software architecture partitioning can occur at this stage. Example EDA software products from Synopsys, Inc. that can be used at this step include Model Architect, Saber, System Studio, and DesignWare® products.

Logic design and functional verification (step 214): At this stage, the VHDL or Verilog code for modules in the system is written and the design is checked for functional accuracy. More specifically, the design is checked to ensure that it produces correct outputs in response to particular input stimuli. Example EDA software products from Synopsys, Inc. that can be used at this step include VCS, VERA, DesignWare®, Magellan, Formality, ESP and LEDA products.

Synthesis and design for test (step 216): Here, the VHDL/Verilog is translated to a netlist. The netlist can be optimized for the target technology. Additionally, the design and implementation of tests to permit checking of the finished chip occurs. Example EDA software products from Synopsys, Inc. that can be used at this step include Design Compiler®, Physical Compiler, DFT Compiler, Power Compiler, FPGA Compiler, TetraMA1, and DesignWare® products.

Netlist verification (step 218): At this step, the netlist is checked for compliance with timing constraints and for correspondence with the VHDL/Verilog source code. Example EDA software products from Synopsys, Inc. that can be used at this step include Formality, PrimeTime, and VCS products.

Design planning (step 220): Here, an overall floor plan for the chip is constructed and analyzed for timing and top-level routing. Example EDA software products from Synopsys, Inc. that can be used at this step include Astro and Custom Designer products.

Physical implementation (step 222): The placement (positioning of circuit elements) and routing (connection of the same) occurs at this step, as can selection of library cells to perform specified logic functions. Example EDA software products from Synopsys, Inc. that can be used at this step include the Astro, IC Compiler, and Custom Designer products.

Analysis and extraction (step 224): At this step, the circuit function is verified at a transistor level, this in turn permits what-if refinement. Example EDA software products from Synopsys, Inc. that can be used at this step include Astro-Rail, PrimeRail, PrimeTime, and Star-RC1T products.

Physical verification (step 226): At this step various checking functions are performed to ensure correctness for: manufacturing, electrical issues, lithographic issues, and circuitry. Example EDA software products from Synopsys, Inc. that can be used at this step include the Hercules product.

Tape-out (step 227): This step provides the "tape out" data to be used (after lithographic enhancements are applied if appropriate) for production of masks for lithographic use to produce finished chips. Example EDA software products from Synopsys, Inc. that can be used at this step include the IC Compiler and Custom Designer families of products.

Resolution enhancement (step 228): This step involves geometric manipulations of the layout to improve manufacturability of the design. Example EDA software products from Synopsys, Inc. that can be used at this step include Proteus, ProteusAF, and PSMGen products.

Mask data preparation (step 230): This step provides mask-making-ready "tape-out" data for production of masks for lithographic use to produce finished chips. Example EDA software products from Synopsys, Inc. that can be used at this step include the CATS® family of products.

Parallel flow. The integrated circuit manufacturing flow includes a parallel flow, as follows:

(1) Develop individual process steps for manufacturing the integrated circuit. This can be modeled with EDA tools such as the Synopsys tools "Sentaurus Process", "Sentaurus Topography", and "Sentaurus Lithography". The input information here is the process conditions like temperature, reactor ambient, implant energy, etc. The output information is the change in geometry or doping profiles or stress distribution.

(2) Integrate the individual process steps into the complete process flow. This can be modeled with EDA tools such as the Synopsys tool "Sentaurus Process". The input information here is the collection of the process steps in the appropriate sequence. The output is the geometry, the doping profiles, and the stress distribution for the transistors and the space in between the transistors.

(3) Analyze performance of the transistor manufactured with this process flow. This can be done with EDA tools such as the Synopsys tool "Sentaurus Device". The input information here is the output of step (3) and the biases applied to transistor terminals. The output information is the currents and capacitances for each bias combination. For silicon based processes or structures, much of the information about the materials needed for simulation of electrical behavior using these tools is well known. For other materials, it may be necessary to generate or provide material parameters like atomic structure, energy, and the like in order to support device and process scale simulations. An EDA tool for generating parameters like this is described herein.

(4) If necessary, modify the process steps and the process flow to achieve the desired transistor performance. This can be done iteratively by using tools such as the Synopsys tools mentioned above.

Once the process flow is ready, it can be used for manufacturing multiple circuit designs coming from different fabless companies. The EDA flow 212-230 will be used by such fabless companies. The parallel flow described here is used at a foundry to develop a process flow that can be used to manufacture designs coming from their fabless customers. A combination of the process flow and the masks 230 are used to manufacture any particular circuit. If the integrated circuit is manufactured at an IDM (integrated device manufacturer) company instead of the combination of a fables company and a foundry, then both parallel flows described above are done at the same IDM company.

FIGS. 13A, 13B, 13C and 13D illustrate various lattice configurations, as examples of arrangements in which a semiconductor property has a finite distortion range to be simulated as in FIGS. 6-8. The finite distortion range can depend on the direction. Distortions can be electrical, mechanical, or band structure. Examples include point defects such as vacancy defects, interstitial defects and substitutional defects, using a GaAs alloy as an example. A conventional 8-atom cell (e.g. 400), and a supercell composed of 8 conventional cells are shown in each of the figures. As used herein, a host is the material into which native defects and dopants diffuse, and a host atom is an atom in the host material without any diffusion into the host material. The host material can be an alloy.

Figure 13A:
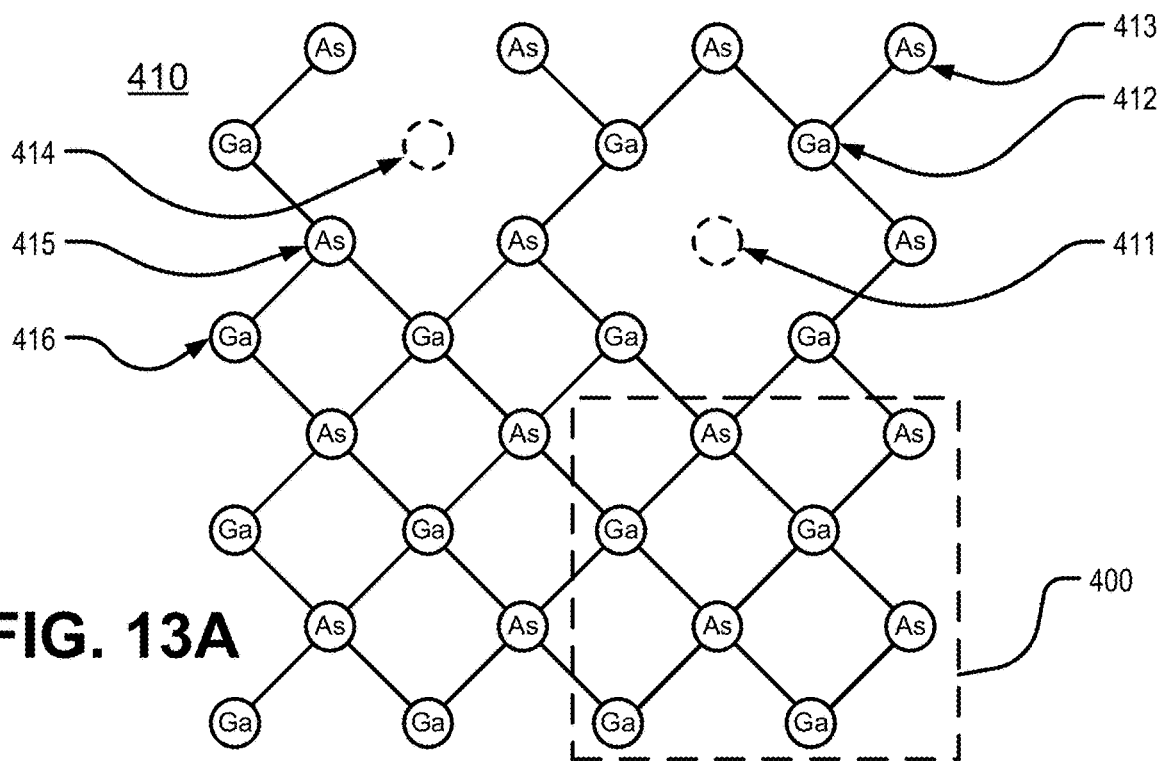
FIGS. 13A, 13B, 13C and 13D illustrate various lattice configurations, as examples of arrangements in which a semiconductor property has a finite distortion range.

FIG. 13A illustrates a supercell 410 including host atoms Ga (Gallium) and As (Arsenic), and lattice vacancy defects (e.g. 411, 414) surrounded by adjacent host atoms Ga and As. A lattice vacancy defect refers to an atom site in a crystal lattice where a single host atom is missing. Neighbors of a point defect can be important. As shown in the example of FIG. 13A, a vacancy defect has first order neighbors and second order neighbors. For instance, vacancy defect 411 at an As site has 4 first-order neighbors that are Ga atoms (e.g. 412), and more second-order neighbors (e.g. 413). Vacancy defect 414 at a Ga site has 4 first-order neighbors that are As atoms (e.g. 415), and more second-order neighbors (e.g. 416).

In a different alloy there can be more options for first-order neighbors. For instance in a SiGe alloy (not shown), a point defect such as a vacancy defect can have different first-order neighbors including 4 Si atoms, 3 Si atoms and 1 Ge atom, 2 Si atoms and 2 Ge atoms, 1 Si and 3 Ge atoms, or 4 Ge atoms.

Figure 13B:
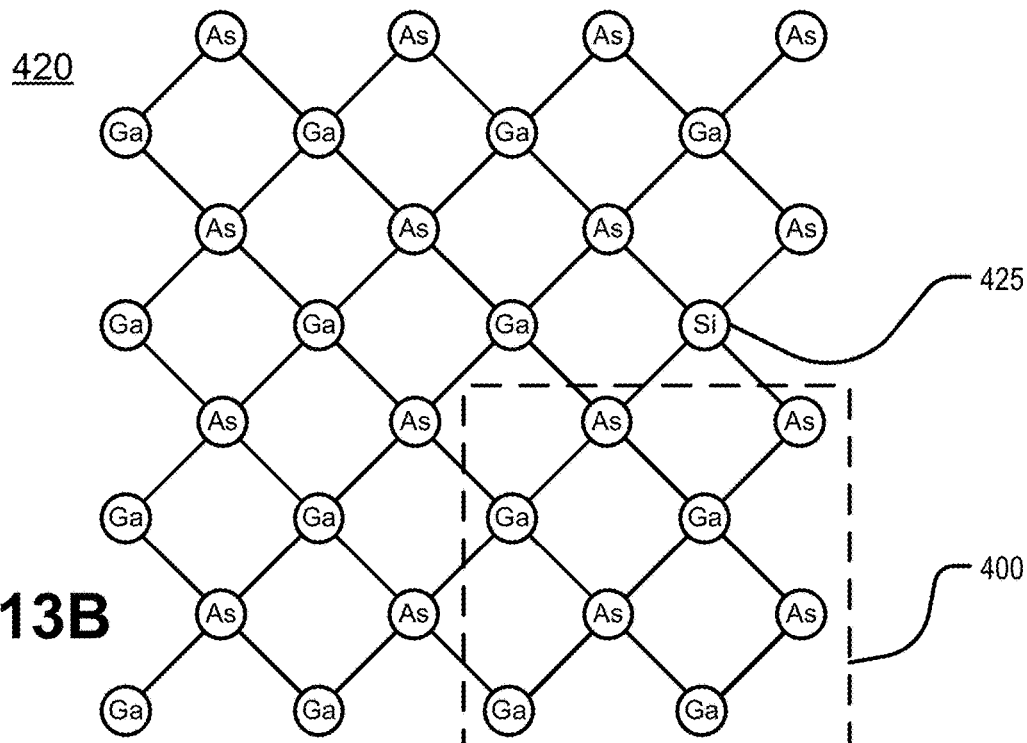

FIG. 13B illustrates an example of a dopant atom surrounded by various different numbers of host atoms adjacent thereto. Impurities or dopants can be doped into the GaAs host material. Group IV elements such as Si (silicon) can act as either donors on Ga sites or acceptors on As sites. In the example of FIG. 13B, Si is used as the dopant (e.g. 425).

Figure 13C:
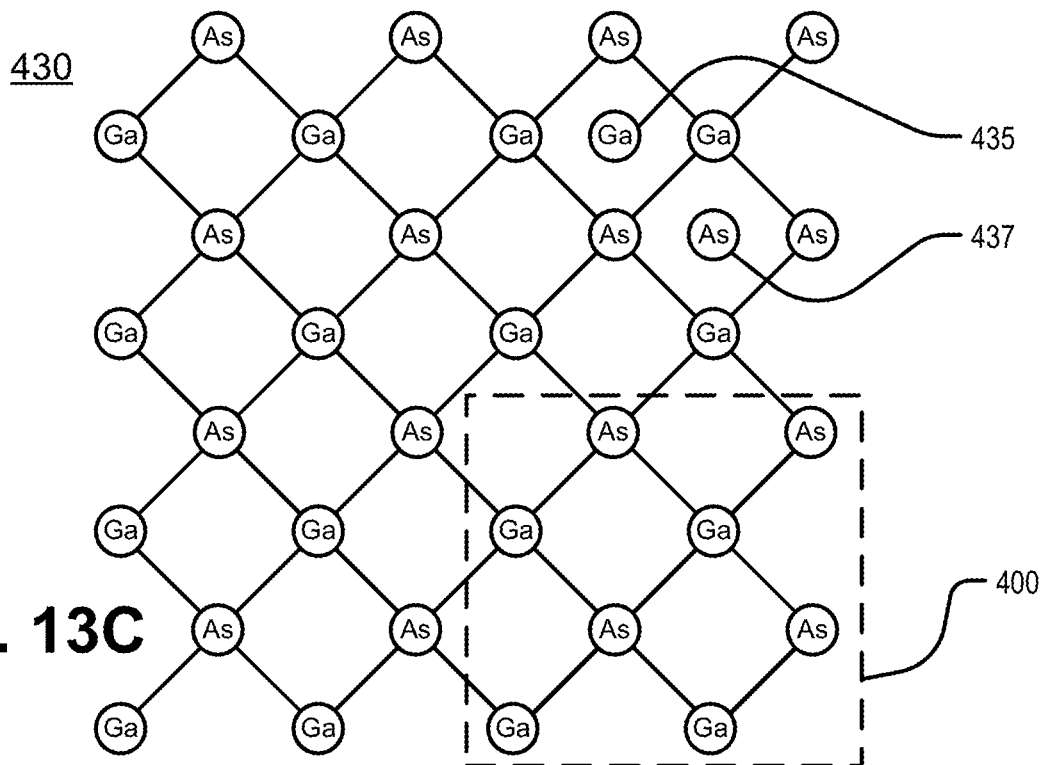

FIG. 13C illustrates an example of an interstitial defect atom surrounded by various different numbers of host atoms adjacent thereto, where an interstitial defect atom is present in the interstitial spaces between the host crystal lattice sites. In an alloy (e.g. GaAs), each alloying species (e.g. Ga, As) can be at a defect site between lattice sites or an interstitial location off the crystal lattice. In the example of FIG. 13C, a Ga interstitial is at a defect site (e.g. 435), while an As interstitial is at another defect site (e.g. 437). In a tetrahedrally coordinated GaAs configuration (not shown), a Ga interstitial or a As interstitial can have four equidistant first-order neighbors. In a hexagonally coordinated GaAs configuration (not shown), a Ga interstitial or a As interstitial can have six equidistant first-order neighbors, including 3 Ga atoms and 3 As atoms.

Figure 13D:
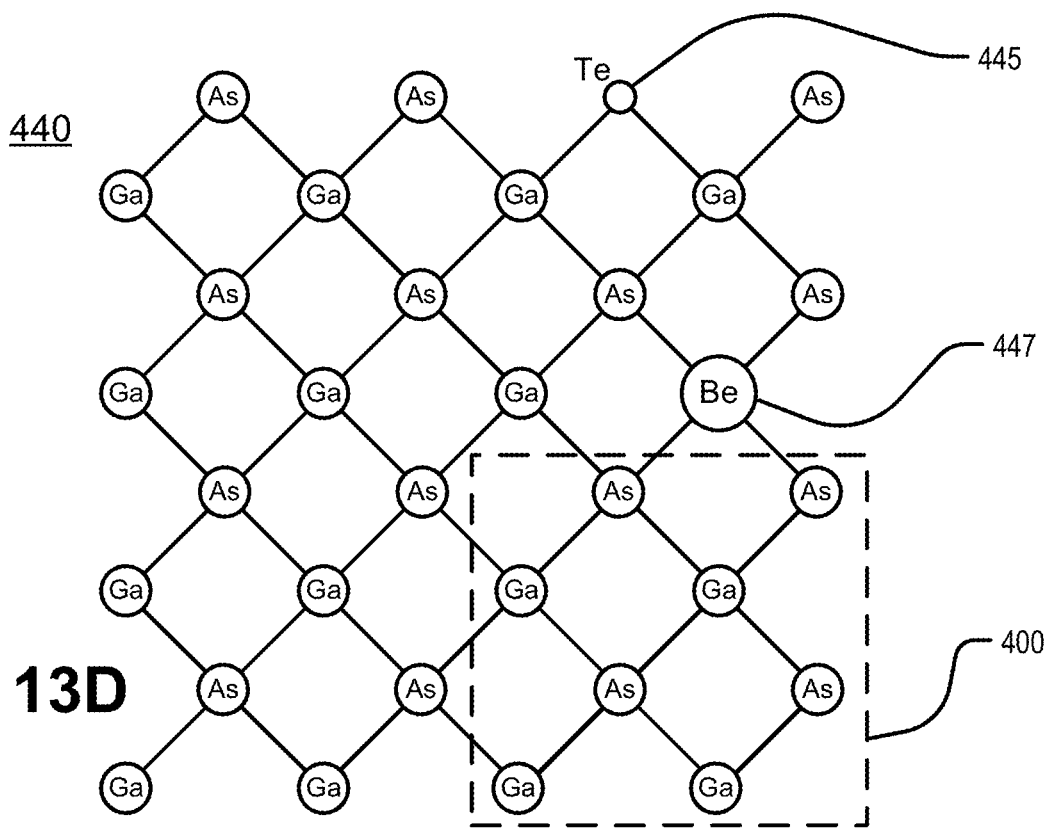

FIG. 13D illustrates an example of a substitutional defect atom surrounded by various different numbers of host atoms adjacent thereto, where a host atom is replaced by an atom of a different type than the host atoms. A substitutional defect atom can be smaller or larger than a host atom (covalent radius of Ga=126 pm, covalent radius of As=119 pm). In the example of FIG. 13D, Be (Beryllium, covalent radius=90 pm) is shown as a smaller substitutional defect atom at a defect site (e.g. 445), while Te (Tellurium, covalent radius=135 pm) is shown as a larger substitutional defect atom at another defect site (e.g. 447).

For a more complex material, there can be more types of point defects. For instance, indium gallium arsenide (InGaAs) is a ternary alloy of indium, gallium and arsenic. Indium and gallium are both from the boron group (group III) of elements, and thus have similar roles in chemical bonding. InGaAs is regarded as an alloy of gallium arsenide and indium arsenide with properties intermediate between the two depending on the proportion of gallium to indium. For instance, compounds In0.75Ga0.25As, In0.5Ga0.5As, and In0.25Ga0.75 include different proportions of gallium to indium, while InAs does not include Ga and GaAs does include In.

In InGaAs, point defects can include As vacancy (i.e. missing lattice atom where As is supposed to be), In/Ga vacancy (i.e. missing lattice atom where In or Ga is supposed to be), As interstitial (i.e. extra As atom between lattice sites), In interstitial (i.e. extra In atom between lattice sites), Ga interstitial (i.e. extra Ga atom between lattice sites), As atom in the In/Ga lattice site, In atom in the As lattice site, and Ga atom in the As lattice site. For each of these point defects, there are different combinations of first-order neighbors, similar to the first-order neighbors described for the SiGe alloy.

Other subject areas include ion intercalation in anodes for rechargeable battery technology such as lithium ion batteries.

Incorporated by reference herein are the following documents, which provide additional information about terms and components referenced herein:

KRESSE, G., et. al., VASP the Guide (Sep. 9, 2013).

The invention claimed is:

1. A system for simulating behavior of structures and materials at multiple scales with different modules, in an evaluation of such structures and materials for use in integrated circuit devices comprising:

a computer system provided with a control module which controls transformations of an atomic structure model into a final state to determine a plurality of ab initio characteristics of the atomic structure as part of an evaluation of structures and materials for use in integrated circuit devices, wherein the control module causes a plurality of ab initio atomic structure relaxation modules to iteratively transform the model of the atomic structure to determine the plurality of ab initio characteristics of the atomic structure, and wherein the plurality of ab initio atomic structure relaxation modules includes:

a first ab initio atomic structure relaxation module responsive to the control module by transforming the model of the atomic structure into a first intermediate state of the model of the atomic structure, based on a conjugate gradient minimization; and a second ab initio atomic structure relaxation module responsive to the control module by transforming the first intermediate state of the model of the atomic structure as previously determined into the final state of the model of the atomic structure, based on a quasi-Newton minimization.

2. The system of claim 1, wherein an iterative transformation of at least one member of the group consisting of the plurality of ab initio atomic structure relaxation modules yields atomic forces of constituent atoms in a unit cell of the atomic structure.

3. The system of claim 1, wherein different iterative transformations of the plurality of ab initio atomic structure relaxation modules, change one or more positions of one or more atoms of the atomic structure as inputs.

4. The system of claim 1, wherein the plurality of ab initio characteristics of the atomic structure includes a plurality of atomic coordinates of constituent atoms in a unit cell of the atomic structure.

5. The system of claim 1, wherein the plurality of ab initio characteristics of the atomic structure includes a minimum energy of a unit cell of the atomic structure.

6. The system of claim 1, wherein the first intermediate state of the model of the atomic structure and the final state of the model of the atomic structure inform ab initio characteristics including at least one member of the group consisting of formation energy of defects, migration energy of defects, entropy of defect formation, entropy of defect migration, defect concentration, and defect diffusivity.

7. The system of claim 1, wherein in causing the plurality of ab initio atomic structure relaxation modules to iteratively transform the model of the atomic structure, the control module indicates to at least one of the first and second ab initio atomic structure relaxation modules a k-mesh resolution to use when conducting the conjugate gradient minimization.

8. A computer executed method of transforming a model of an atomic structure into a final state to determine a plurality of ab initio characteristics of the atomic structure, using a computer system provided with a control module which controls transformations of an atomic structure model into a final state to determine a plurality of ab initio characteristics of the atomic structure, the method comprising:
the control module causing a plurality of ab initio atomic structure relaxation modules to iteratively transform the model of the atomic structure to determine the plurality of ab initio characteristics of the atomic structure, including:
the control module causing a first ab initio atomic structure relaxation module to transform the model of the atomic structure into a first intermediate state of the model of the atomic structure, based on a conjugate gradient minimization; and
the control module causing a second ab initio atomic structure relaxation module to transform the first intermediate state of the model of the atomic structure as previously determined into the final state of the model of the atomic structure, based on a quasi-Newton minimization.

9. The method of claim 8, wherein an iterative transformation of at least one member of the group consisting of the plurality of ab initio atomic structure relaxation modules yields atomic forces of the atomic structure.

10. The method of claim 8, wherein different iterative transformations of the plurality of ab initio atomic structure relaxation modules change one or more positions of one or more atoms of the atomic structure as inputs.

11. The method of claim 8, wherein the plurality of ab initio characteristics of the atomic structure includes a plurality of atomic coordinates of a plurality of constituent atoms in a unit cell of the atomic structure.

12. The method of claim 8, wherein the plurality of ab initio characteristics of the atomic structure includes a minimum energy of a unit cell of the atomic structure.

13. The method of claim 8, wherein the first intermediate state of the model of the atomic structure and the final state of the model of the atomic structure inform ab initio characteristics including at least one member of the group consisting of formation energy of defects, migration energy of defects, entropy of defect formation, entropy of defect migration, defect concentration, and defect diffusivity.

14. The method of claim 8, wherein in causing the plurality of ab initio atomic structure relaxation modules to iteratively transform the model of the atomic structure, the control module indicates to at least one of the first and second ab initio atomic structure relaxation modules a k-mesh resolution to use when conducting the conjugate gradient minimization.

15. The method of claim 8, wherein the computer causing a first ab initio atomic structure relaxation module to transform the model, comprises the computer the computer causing the first ab initio atomic structure relaxation module to transform the model using a first k-mesh resolution,
and wherein the computer causing a second ab initio atomic structure relaxation module to transform the previously determined intermediate state of the model, comprises the computer causing the second ab initio atomic structure relaxation module to transform the previously determined intermediate state of the model using a second k-mesh resolution which is higher than the first k-mesh resolution.

16. The method of claim 15, wherein the previously determined intermediate state of the model is the first intermediate state of the model.

17. The method of claim 15, wherein the first k-mesh resolution has either a single gamma point in a Brillouin zone of the atomic structure or a 2×2×2 k-mesh in the Brillouin zone of the atomic structure.

18. A non-transitory computer readable medium having stored thereon a plurality of software code portions defining logic for simulating behavior of structures and materials at multiple scales with different modules, in an evaluation of such structures and materials for use in integrated circuit devices, comprising:
software code portions defining logic for a control module which controls transformations of an atomic structure model into a final state to determine a plurality of ab initio characteristics of the atomic structure as part of an evaluation of structures and materials for use in integrated circuit,
wherein the control module controls a plurality of ab initio atomic structure relaxation modules to iteratively transform the model of the atomic structure to determine the plurality of ab initio characteristics of the atomic structure,
and wherein the plurality of ab initio atomic structure relaxation modules include:
a first ab initio atomic structure relaxation module responsive to the control module by transforming the model of the atomic structure into a first intermediate state of the model of the atomic structure, based on a conjugate gradient minimization; and a second ab initio atomic structure relaxation module responsive to the control module by transforming the first intermediate state of the model of the atomic structure as previously determined into the final state of the model of the atomic structure, based on a quasi-Newton minimization.

19. A system for simulating behavior of structures and materials at multiple scales with different modules, in an evaluation of such structures and materials for use in integrated circuit devices, for use with a plurality of ab initio atomic structure relaxation modules, the system transforming a model of an atomic structure into a final state to determine a plurality of ab initio characteristics of the atomic structure, comprising:

a controller which controls the ab initio atomic structure relaxation modules to iteratively transform the model of the atomic structure to determine the plurality of ab initio characteristics of the atomic structure, the controller including:

a module for controlling a first ab initio atomic structure relaxation module to transform the model of the atomic structure into a first intermediate state of the model of the atomic structure, based on a conjugate gradient minimization, the module also controlling a second ab initio atomic structure relaxation module to transform the first intermediate state of the model of the atomic structure as previously determined into the final state of the model of the atomic structure, based on a quasi-Newton minimization.

\* \* \* \* \*